(12) United States Patent
Rivier et al.

(10) Patent No.: US 12,383,365 B2
(45) Date of Patent: Aug. 12, 2025

(54) SYSTEM AND METHOD FOR TRACKING DATA RELATING TO THE PROCESSING OF MEDICAL CONTAINERS

(71) Applicant: Becton Dickinson France, Le Pont de Claix (FR)

(72) Inventors: Cédric Rivier, Voreppe (FR); Nicolas Euvrard, Durham, NC (US)

(73) Assignee: Becton Dickinson France, Le Pont de Claix (FR)

( * ) Notice: Subject to any disclaimer, the term of this patent is extended or adjusted under 35 U.S.C. 154(b) by 227 days.

(21) Appl. No.: 17/624,053

(22) PCT Filed: Jun. 29, 2020

(86) PCT No.: PCT/EP2020/068303
§ 371 (c)(1),
(2) Date: Dec. 30, 2021

(87) PCT Pub. No.: WO2021/001325
PCT Pub. Date: Jan. 7, 2021

(65) Prior Publication Data
US 2022/0354609 A1      Nov. 10, 2022

(30) Foreign Application Priority Data
Jul. 1, 2019 (EP) .................................... 19305896

(51) Int. Cl.
*A61B 50/39* (2016.01)
*G06K 7/10* (2006.01)

(52) U.S. Cl.
CPC .......... *A61B 50/39* (2016.02); *G06K 7/10237* (2013.01)

(58) Field of Classification Search
CPC ... A61B 50/39; G06K 7/10237; B65D 5/4212
USPC ........... 206/570, 569, 535, 459.1, 562, 564, 206/459.5, 571
See application file for complete search history.

(56) References Cited

U.S. PATENT DOCUMENTS

| 10,307,548 | B1 | 6/2019 | Hunt et al. |
| 2005/0100483 | A1 | 5/2005 | Guiney |
| 2012/0025988 | A1 | 2/2012 | Harada |
| 2012/0316987 | A1 | 12/2012 | Debusk et al. |

(Continued)

FOREIGN PATENT DOCUMENTS

| CN | 1545681 A | 11/2004 |
| CN | 101219072 A | 7/2008 |

(Continued)

*Primary Examiner* — Rafael A Ortiz
(74) *Attorney, Agent, or Firm* — The Webb Law Firm

(57) ABSTRACT

A system for tracking data relating to the processing of a plurality of medical containers adapted to be received in a first layer of a packaging, the system including: at least one mark being implemented on and/or within the material of each medical container and representing a corresponding unique device identifier (UDI) for each respective medical container, a remotely readable and writable electronic component (21) which is on and/or within the first layer of packaging, the remotely readable and writable electronic component being configured for storing the UDI of each medical container received in the first layer of packaging and for writing and/or reading data relating to the processing of the medical containers.

18 Claims, 4 Drawing Sheets

(56) References Cited

U.S. PATENT DOCUMENTS

| | | | |
|---|---|---|---|
| 2014/0223862 A1 | 8/2014 | Nicoletti et al. | |
| 2014/0258165 A1* | 9/2014 | Heil | G06Q 10/0833 235/494 |
| 2015/0004582 A1* | 1/2015 | Baker | G09B 19/00 434/262 |
| 2015/0028997 A1* | 1/2015 | Phillips | H04W 4/029 340/8.1 |
| 2015/0029001 A1 | 1/2015 | Pleshek et al. | |
| 2015/0091705 A1 | 4/2015 | Banegas et al. | |
| 2015/0108034 A1* | 4/2015 | Deutschle | A61J 1/16 206/593 |
| 2015/0122693 A1* | 5/2015 | Deutschle | B65D 1/36 53/471 |
| 2015/0176055 A1 | 6/2015 | Knapp, Jr. et al. | |
| 2015/0197372 A1* | 7/2015 | Majlof | G06K 19/06028 427/256 |
| 2016/0206806 A1* | 7/2016 | Wright | A61M 5/24 |
| 2016/0275323 A1 | 9/2016 | Johanson et al. | |
| 2018/0369820 A1* | 12/2018 | Kaneko | B01L 9/523 |

FOREIGN PATENT DOCUMENTS

| | | | | |
|---|---|---|---|---|
| JP | 2008535569 A | 9/2008 | | |
| JP | 2016073377 A | 5/2016 | | |
| JP | 6462947 B1 | 1/2019 | | |
| RU | 2013150137 A | 5/2015 | | |
| WO | 2006108026 A2 | 10/2006 | | |
| WO | WO-2016166765 A1 * | 10/2016 | | A61J 1/062 |
| WO | WO-2017157784 A1 * | 9/2017 | | B01L 3/545 |
| WO | 2018093706 A1 | 5/2018 | | |
| WO | 2019020974 A1 | 1/2019 | | |

\* cited by examiner

SYSTEM AND METHOD FOR TRACKING DATA RELATING TO THE PROCESSING OF MEDICAL CONTAINERS

CROSS-REFERENCE TO RELATED APPLICATIONS

This application is the United States national phase of International Application No. PCT/EP2020/068303 filed Jun. 29, 2020, and claims priority to European Patent Application No. 19305896.3 filed Jul. 1, 2019, the disclosures of which are hereby incorporated by reference in their entirety.

BACKGROUND OF THE DISCLOSURE

The disclosure relates to a system and a method for tracking data relating to the processing of one or more medical containers such as syringes, vials or cartridges.

DESCRIPTION OF RELATED ART

Often, medical containers must be transported from one site to another, when they are manufactured in one site and filled in another site, or, less frequently, when they are manufactured and filled in the same site and must be delivered, once filled, to another site.

For this transportation, the containers are usually put in a packaging comprising a grouping tray or nest, hereinafter "nest", a packaging tub, hereinafter "tub", and preferably a sealing cover and a plastic bag, hereinafter "header bag" to ensure the sterility. The combination of the nest and the tub, and optionally the sealing cover and the header bag, will be cited hereinafter as "packaging" while the term "tub" will correspond to an empty tub.

The nest can have various shapes according to the type of containers received. It can comprise openings that can be or not coaxially surrounded by chimneys for receiving the cylindrical bodies of the containers with flanges, these flanges leaning on the upper ends of the chimneys. Alternatively, the nest can have specific openings for receiving cartridges that would be in contact with the bottom of the tub. In another embodiment, the nest can have chimneys with closed bottoms for receiving containers without flanges; the nest can also be made of a resilient material and have openings in which the containers are frictionally maintained.

The nest is therefore made for easily storing and transporting several containers at the same time without risks of contamination or breakage. Besides, this storage and transportation means can be used and re-used from the manufacture of the containers until their final filling and storage by the pharmaceutical industry.

The tub includes a peripheral outer flange levelled with its upper opening, for the sealing of the sealing cover. The tub also includes a peripheral inner flange, located below the outer flange, in order to support the nest. In use, the nest is placed into the tub which is sealed with a sealing cover, and the whole is enclosed in the header bag and sterilized. Then, series of packages may be stacked bottom up into a box, for example, a cardboard or a plastic box, with an intermediate sheet placed between two series of packaging's, a series being defined as a row of several packaging's.

When received at destination, the packages are extracted from the box and flipped bottom down, the header bag is open, the tub is extracted from the header bag and unsealed. Then, the nests are extracted therefrom and the containers can be filled and/or handled.

A major point with regards to the manufacture, transportation, and filling of the medical containers, that will be mentioned hereinafter as "processing", is the tracking of the medical containers, i.e. the ability to identify each of the medical containers all along the processing chain, from their manufacture in the manufacturer, including their packaging in a nest and then in a tub, to their filling and further processing, usually in a final customer of the manufacturer. The tracking of the medical containers may also be advantageous up to their final use, for example injection to a patient, and even further to their disposal.

Solutions have been proposed to achieve tracking of the medical containers.

A first solution consists of marking the medical containers with a data tag or label. Each data tag differs from one container to the other, thereby making it possible to individually track each container.

The customer may ensure traceability at the container level, for example by using color labelling which may be quite difficult to implement, and/or by performing laborious manual procedures during line clearance or manual reconciliation of the containers. In particular, color labelling can be performed only on the external diameter of the container, close to the flange, and is very likely to be degraded during sterilization operations.

In addition, marking of the container is not visible when said container is packaged in the tub, or in the nest, such nest being generally used as a conveyor during the processing of the containers by the customer. Hence, the customer cannot see the marking and cannot identify the containers, which severely limits the tracking of the containers and may lead to errors during the filling of the containers when a given composition is filled in the wrong container.

A second solution consists of marking the nest which carries the medical containers, said containers being not marked.

However, before the containers are arranged in the nest, there is no traceability at the container level. Moreover, when the customer removes the medical containers from the nest for performing a quality check of said containers and filling them with a composition, the traceability of the containers is lost. As a consequence, the customer cannot ensure that the right container has been filled with the right composition, which may lead to severe consequences onto a patient to be treated with the composition.

SUMMARY OF THE DISCLOSURE

The disclosure aims to provide a system for tracking data relating to the processing of one or more medical containers adapted to be received in a nest of a packaging, that allows for efficiently tracking each of said medical containers all along the processing chain, from their manufacture in the manufacturer, including their packaging in a nest and then in a tub, their filling and further processing, usually in a final customer of the manufacturer, and event further typically during the use of the medical containers, for example for injecting a pharmaceutical composition, and their disposal.

To this end, an object of the disclosure is a system for tracking data relating to the processing of a plurality of medical containers adapted to be received in a first layer of a packaging, the system comprising:

at least one mark being implemented on and/or within the material of each medical container and representing a corresponding unique device identifier (UDI) for each respective medical container, a remotely readable and writable electronic component comprised on and/or within the first layer of packaging, said remotely readable and writable electronic component being configured for storing the UDI of each medical container received in the first layer of packaging and for writing and/or reading data relating to the processing of the medical containers.

A packaging, especially for medical containers, may comprise a plurality of layers that separate the containers from the outside environment. Some of said layers may be configured to form a barrier to air, fluids, and/or any contaminant that may affect the sterility of the containers. Some of said layers may be configured to protect the medical containers from shocks and/or vibrations that could affect their integrity. In the present text, the "first layer" designates a layer of the packaging that is closer to the medical containers. In particular, said first layer is in contact with the atmosphere that surrounds the medical containers. Said first layer is also, chronologically, one of the first layers used in the packaging process.

The expression "comprised on and/or within" means that the component may be included in the first layer of packaging and/or attached thereto, by any suitable means (e.g. overmolded, labeled, glued, assembled by mechanical fixation means such as clips, screws, etc.).

The system for tracking data of the disclosure allows full traceability of a drug container from the first steps of the process to the pharmaceutical customer at final packaging step by combining the marking of the medical containers, said marking of each medical container comprising a Unique Device Identifier (UDI), with a remotely readable and writable electronic component embedded in a nest.

The marking of the medical containers is made on the material, or within the bulk material of said medical containers, during their manufacture. Preferably the marking of the medical containers is made within the bulk of said medical containers. This marking is robust and may be made as early as possible during the manufacturing of the medical containers.

In the present text, the "bulk material" corresponds to the material that constitutes the body or a cap of a medical container. The material may be glass, plastic, rubber or thermoplastic elastomer.

In the present text, the term "robust" means that the marking will resist to any step of the manufacturing process of the medical containers.

The proposed system for tracking data hence combines container traceability without visual reading constraints, as said containers are virtually aggregated to the remotely readable and writable electronic component of the nest. Furthermore, the nest UDI is accessible without visual reading constraint, as it may be read via wireless technology of the remotely readable and writable electronic component, such as a RFID tag.

According to other optional features of the system for tracking data:
the first layer of packaging is a nest or a tub, preferably a nest,
the remotely readable and writable electronic component comprises a corresponding unique device identifier (UDI) relating to the first layer of packaging;
the system for tracking data further comprises a data storage system configured for storing data relating to the processing of the medical container, said data being associated with the UDI of each medical container and optionally with the UDI of the first layer of packaging;
the at least one mark is optical, preferably selected from the group consisting of a 1D mark, such as a bar code, a 2D mark such as a Data Matrix or a QR code, and a text;
the remotely readable and writable electronic component is selected from the group consisting of a RFID tag, an ultra wide-band real-time location system (RTLS), a wifi-enabled module, a Bluetooth-enabled module, a ZigBee-enabled module and an infrared-enabled module, preferably the remotely readable and writable electronic component is a RFID tag which comprises an RFID chip and an antenna connected to the chip.

Another object of the disclosure is a method for tracking data relating to the processing of a plurality of medical containers adapted to be received in a first layer of a packaging, said method comprising the steps of:
a) providing a material for processing a plurality of medical container,
b) implementing a mark on and/or within the material of each medical container during the first steps of the manufacturing of the medical containers, said mark encoding a corresponding unique device identifier (UDI) for each respective medical container, and further comprising, during each manufacturing steps of the medical containers the following step:
c) writing data relative to the manufacturing steps of the medical containers and/or individual physical data of each medical container in a data storage system, said written data being associated with the UDI of each respective medical container.

According to other optional features of the method for tracking data:
the method further comprises:
d) placing the medical containers implemented with a mark into the first layer of packaging comprising a remotely readable and writable electronic component,
e) writing of the UDI of each medical container in the remotely readable and writable electronic component comprised on and/or within the first layer of packaging,
and further comprising, during each processing steps of the first layer of packaging, the following step:
f) writing data relating to said each processing step of the first layer of packaging in the data storage system and optionally in the remotely readable and writable electronic component comprised in the first layer of packaging;
the marking of the medical containers is made by labelling, enamel sintering, inkjet printing, laser marking such as picosecond laser marking or femtosecond laser marking, drop-on demand printing, or dot peen marking;
the manufacturing steps of the medical container may be at least one of the followings:
i) cutting, washing and forming a glass cane which is used as a raw material for the medical container,
ii) molding a plastic used as a raw material for the medical container,
iii) scale printing the medical container,
iv) assembling a needle onto the medical container,
v) washing the medical container,
vi) siliconizing the medical container,
vii) assembling a tip cap onto the medical container,
viii) visually inspecting the medical container;
the data written in step c) and/or f) are selected from the following: setting, date, station identifier, external temperature, and/or raw material batch number;

the data storage system comprises at least one computer server and/or at least one storage drive;
the processing steps of the first layer of packaging may be at least one of the following:
sterilizing the first layer of packaging and each of the medical containers arranged in the first layer of packaging,
stoppering each of the medical containers,
storing the nest into a tub for intermediate storage and/or shipment.

In some embodiments, the first layer of packaging is a nest and the processing of the first layer of packaging further comprises at least one of the following steps:
filling each medical container arranged in the first layer of packaging with a pharmaceutical composition;
conveying the first layer of packaging to an inspection spot wherein each of the medical containers may be inspected.

BRIEF DESCRIPTION OF THE DRAWINGS

Further features and advantages of the disclosure will be disclosed in the following description, based on the appended drawings, wherein.

DETAILED DESCRIPTION

The disclosure relates to a system for tracking data relating to the processing of at least one medical container adapted to be received in a first layer of a packaging.

The medical container may be a syringe, a vial or a cartridge. The medical container may include a barrel and a cap covering a tip of the barrel.

The first layer of the packaging may be a nest configured to maintain the at least one medical container in a determined position and/or orientation, or a tub containing such a nest. According to a preferred embodiment, the first layer is the nest.

Figure 1:
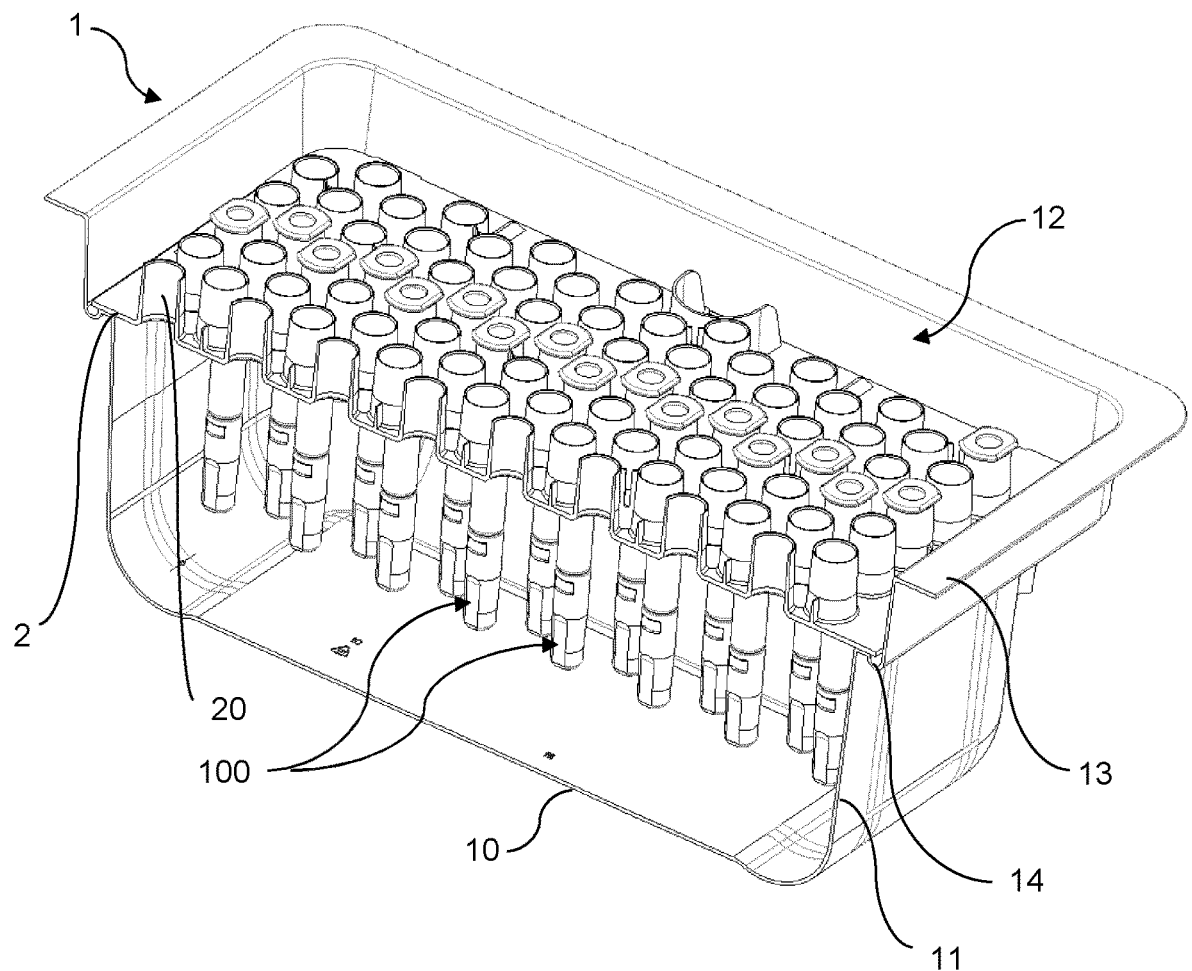
FIG. 1 is a partial cut of a packaging for medical containers comprising a nest and a tub.

FIG. 1 illustrates an embodiment of such a packaging.

The packaging comprises a tub 1, which is generally made of a plastic material, which is configured to enclose a plurality of medical containers 100. The tub comprises a bottom 10, a peripheral wall 11 extending from the bottom to a top opening 12 of the tub. A peripheral flange 13 extends outwardly from the top of the peripheral wall 11. The peripheral flange is configured to be sealed to a sealing cover (not shown) to sealingly close the tub.

Advantageously, the medical containers 100 may be arranged vertically in the tub, i.e. the longitudinal axis of the barrel of the medical container extends in a vertical direction (which is the direction of gravity), with an opening of the barrel directed toward the top of the tub. In this orientation, the medical containers may thus be filled with a pharmaceutical composition while remaining in the tub, thereby minimizing handling of the medical containers.

To that end, the medical containers 100 may be placed in a nest 2, which comprises a plurality of guiding holes 20 configured to receive a respective medical container and maintain it in the vertical direction. The tub 1 comprises a peripheral internal rim 14 configured to support the nest 2.

In other embodiments (not represented), the medical containers may be arranged in a different orientation in the tub, e.g. in a horizontal direction, but this orientation is less preferred since it does not allow filling the medical containers directly in the tub.

Figure 2:
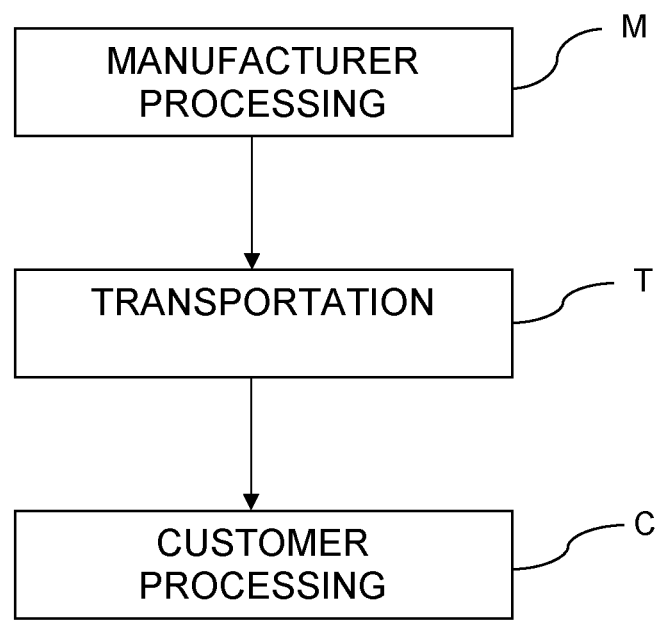
FIG. 2 illustrates a typical workflow of processing of medical containers.

The term "processing" refers to the steps involving the medical containers, from their manufacture by the manufacturer and their arrangement in the first layer of the packaging, to the final packaging by the customer after the medical containers have been inspected by the customer. A first part M of the processing, referred to as "manufacturer processing", may be performed by the manufacturer, and a second part C of the processing, referred to as "customer processing", may be performed by a customer or successively by a plurality of customers. The processing also includes the transportation T of the first layer of packaging containing the medical containers from the manufacturer to the customer (see FIG. 2). The steps performed in the manufacturer processing and those performed in the customer processing will be described in more details in the following text.

The present disclosure aims to ensure a clear and complete traceability of the medical containers from their manufacture by the manufacturer and packaging in the first layer to the customer at a final packaging step, and even further up to the disposal of the medical containers.

In order to do so, the disclosure provides a system for tracking data that combines at least one medical container marked with an identifier specific to said at least one medical container with a remotely readable and writable electronic component embedded in the first layer of packaging intended to receive these marked medical containers.

In more details, the system for tracking data comprises at least one mark associated with each medical container, said mark being implemented on each medial container during the manufacturing process of said medical container, and a remotely readable and writable electronic component embedded in the first layer of packaging.

Figure 3A:
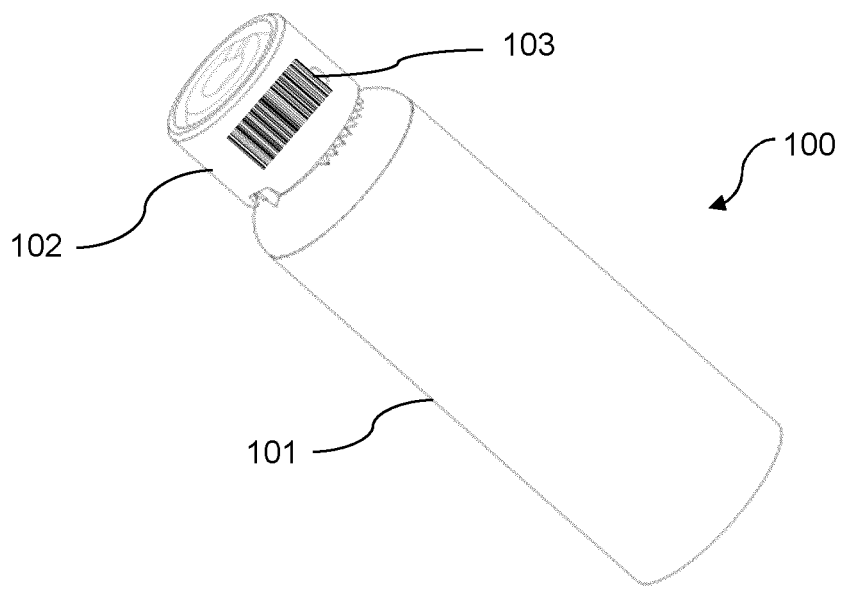
FIG. 3A represents a medical container comprising a bar code marked on a tip cap.
Figure 3B:
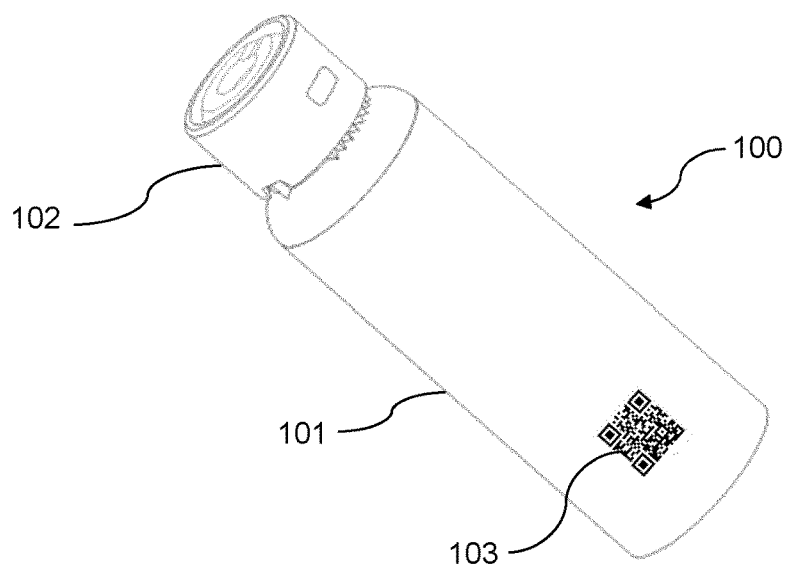
FIG. 3B represents a medical container comprising a QR code marked on the body of the medical container.

FIGS. 3A and 3B illustrate embodiments of a medical container 100, which comprises a barrel 101 and a cap 102 covering a tip of the barrel.

Each medical container is implemented with a corresponding mark 103. This mark represents a corresponding unique device identifier, acronym UDI, that allows for the identification of a respective medical container among the others. In that way, each container comprises a unique and respective UDI that contains information, specific to that container, and thus may be tracked during the whole processing of the medical containers.

Preferably, the mark is selected from the group consisting of a one-dimensional (1D) mark, a two-dimensional (2D) mark or a text. Advantageously, the mark 103 is selected from the group consisting of a bar code (see FIG. 3A), a Data Matrix, a QR code (see FIG. 3B) or a text. Advantageously, the mark is a Data Matrix. The Data Matrix is a two-dimensional high-density barcode symbology, which allows for integrating a large amount of information, or data, on a small area, such as the barrel of a medical container. As such, the Data Matrix is particularly adapted for the marking of the medical containers.

The type of marking is preferably selected among the following: labelling, enamel sintering, inkjet printing, laser marking such as picosecond laser marking or femtosecond laser marking, drop-on demand printing, or dot peen marking.

This mark may be implemented on the surface of the material of the medical container, or within the bulk material of the medical container. Preferably, the mark is implemented within the bulk material of the medical container. If the medical container comprises a barrel 101 and a cap 102 covering a tip of the barrel, the mark may be formed on or in the bulk material of the cap 102 (see FIG. 3A) and/or on or in the bulk material of the barrel 101 (see FIG. 3B).

The remotely readable and writable electronic component, comprised on and/or within the first layer of packaging, is configured for writing and reading data relating to the processing of the medical containers intended to be contained therein. Said remotely readable and writable electronic component may also comprise a corresponding unique device identifier (UDI) relating to the first layer of packaging.

The remotely readable and writable electronic component may be selected from the group comprising a RFID tag, a ultra wide-band real-time location system (RTLS), a wifi-enabled module, a Bluetooth™-enabled module, a ZigBee™-enabled module and an infrared-enabled module. Preferably, the remotely readable and writable electronic component is a RFID (Radio Frequency Identification) tag. Said RFID tag comprises a RFID chip and an antenna connected to the chip. The RFID tag is known per se, and is quite readily usable as for example in the form of a self-adhesive label, which can be adhered to an object, or in the form of a self-supported device that may be incorporated into an object, especially a first layer of packaging according to the present disclosure, e.g. by overmolding.

According to an embodiment, the remotely readable and writable electronic component is embedded into the first layer of packaging. By electronic component embedded in the first layer of packaging it should be understood that the nest fully or at least partially encases the electronic component, so that the electronic component is protected from the external environment and therefore cannot be damaged or removed. As such, the remotely readable and writable electronic component cannot be physically accessed, which prevents any damage that could arise from the steps of the processing, especially during the transportation of the nest containing the medical containers from the manufacturer to the customer, or during the sterilization processes such as ethylene oxide or steam sterilization.

According to an embodiment, the remotely readable and writable electronic component is associated with a processor and/or at least one sensor, which are also embedded in the first layer of packaging. The sensor may be selected among one or more of the following: a temperature sensor, a pressure sensor, a humidity sensor, and a movement sensor. The remotely readable and writable electronic component may further be associated with a battery to power the above-mentioned elements, and a memory for storing data. The remotely readable and writable electronic component may further be associated with a GPS module (Global Positioning System) for locating the nest during the processing of the medical containers.

The sensors are configured to input physical data relative to their respective function, such as temperature, pressure, humidity, and movement data, and to output a corresponding signal to the processor, during the processing of the medical containers. After processing of the signal, the data may be stored in the memory and/or transferred to the data storage system.

Figure 4:
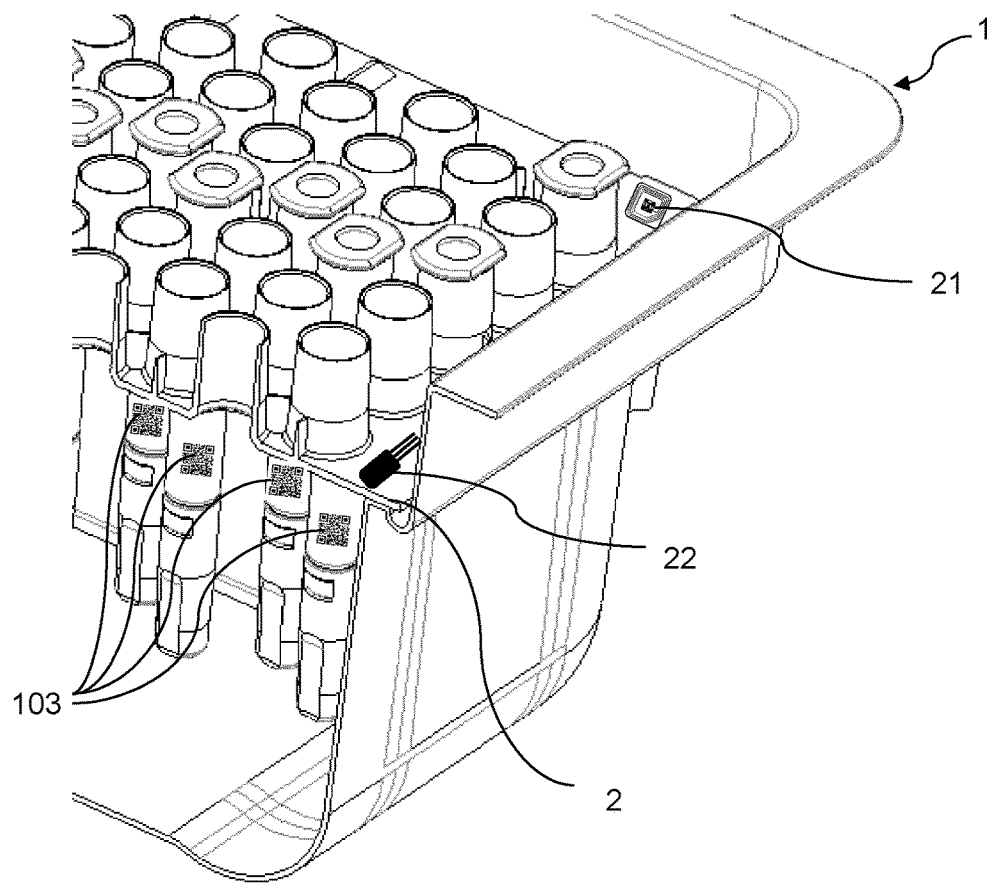
FIG. 4 is a partial view of a nest comprising an RFID tag and a temperature sensor.

FIG. 4 illustrates an embodiment of a nest 2 comprising an RFID tag 21 and a temperature sensor 22. The RFID tag and the temperature sensor may be included within the material of the nest, e.g. by overmolding in the plastic material of the nest, or attached to the upper or lower surface of the nest, e.g. using an adhesive.

According to a preferred embodiment, the system for tracking data further comprises a data storage system, in which the data relating to the UDI of each medical container, to the UDI of the nest, and/or the data written in the remotely readable and writable electronic device may be stored.

Preferably, the data storage system comprises a computer server and/or a storage drive. Advantageously, the data storage system may comprise several computer server and/or several storage drives.

In the case of a storage drive, the manufacturer may transfer manufacturer processing data to the storage drive, and provide the storage drive to the customer. Hence, the customer may access the storage drive and review the data, thereby allowing him to check the conformity of the manufacturer processing with standards.

In the case of a computer server, the manufacturer may transfer manufacturer processing data to the server. The customer may then access the server and review the data, in particular for conformity check. The customer may also transfer customer processing data to the server.

The access to the data granted by the manufacturer to the customer may be total, meaning that the customer may access the full data stored in the storage data system, or partial, meaning that the customer may access only a part of the data stored in the storage data system.

Moreover, in addition to the review of the data, the customer may use these data and implement them in the customer chain.

According to a first embodiment, a computer server is shared between the manufacturer and the customer. The manufacturer and the customer may exchange data with each other.

According to a second embodiment, the manufacturer may access a first server, called manufacturer server, and the customer may access a second server, called customer server. The manufacturer may transfer manufacturer processing data to the manufacturer server, and transfer these data, or part of them, to the customer server. The customer may then access the customer server to review these data. The customer may transfer customer processing data to the customer server, and transfer these data, or part of them, to the manufacturer server.

An example of the computer server may be of a "cloud" type.

Figure 5:
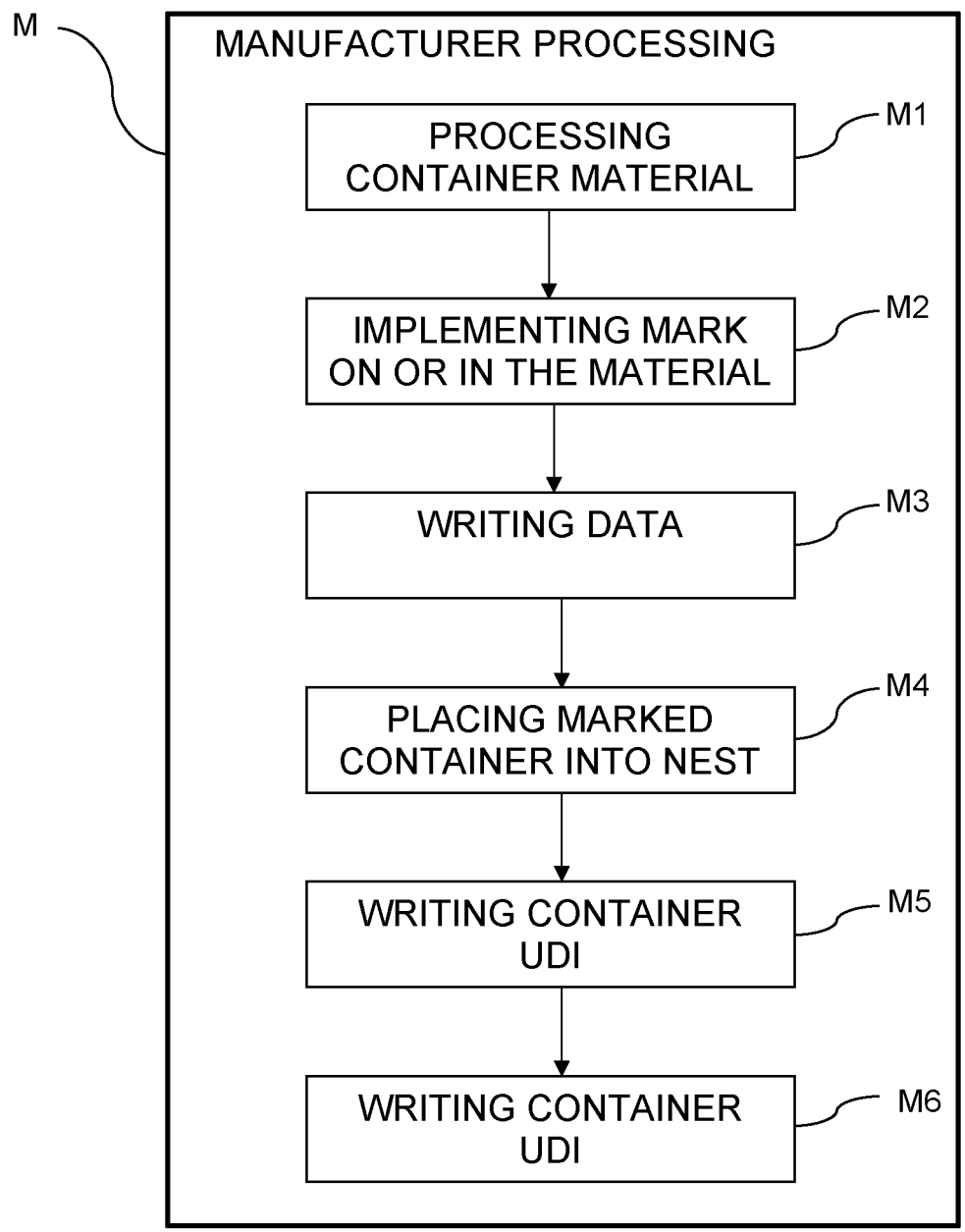
FIG. 5 is a typical workflow of processing of medical containers at the manufacturer's plant.

The disclosure also relates to a method for tracking data relating to the processing of a plurality of medical containers adapted to be received in a nest, said method comprising the steps of (see FIG. 5):

a) step M1: providing a material for processing a plurality of medical container, b) step M2: implementing a mark on and/or within the material of each medical container during the first steps of the manufacturing of the medical containers, said mark encoding a corresponding unique device identifier (UDI) for each respective medical container;

and further comprising, during each manufacturing steps of the medical containers the following step:

c) step M3: writing data relative to the manufacturing steps of the medical containers and/or individual physical data of each medical container in a data storage system, said written data being associated with the UDI of each respective medical container.

As explained above, the step M2 may be implemented by labelling, enamel sintering, inkjet printing, laser marking such as picosecond laser marking or femtosecond laser marking, drop-on demand printing, or dot peen marking, preferably by laser marking.

Before step M3, an additional comparison step may be implemented. Said comparison step enables comparing the data associated to the UDI of each medical container with a reference identifier in order to ensure that the compared medical container is the one sought, for instance the one identified on the manufacturing order. Whether the comparison step is negative, another comparison step may occur. Whether the comparison step is positive, step c) may be implemented.

Step M3 may occur during each manufacturing steps of the medical containers. Thus step M3 may either occur at the beginning, in the middle or at the end of the manufacturing step.

During step M3, any data relating to the manufacturing steps and to the UDI of the medical container may be written in the data storage system. These data may be settings, date, station identifier, external temperature, raw material batch number, and also preferably dimensional and cosmetic defects provided by a control camera during bulk process, type of apparatuses used, etc.

The method of the disclosure may further comprise the following steps (see FIG. 5):
  d) step M4: placing the medical containers implemented with a mark into a nest comprising a remotely readable and writable electronic component,
  e) step M5: writing of the UDI of each medical containers in the remotely readable and writable electronic component comprised in the nest.

The method of the disclosure may further comprise, during each processing steps of the nest, the following step:
  f) step M6: writing data relating to said each processing step of the nest in the data storage system and optionally in the remotely readable and writable electronic component comprised in the nest.

In the method of the disclosure, the manufacturing steps of the medical containers may comprise at least one of the following steps: cutting, washing, forming the glass canes or molding the plastic materials which are used as a raw material for the medical container, printing of a scale such as a volumetric scale, annealing glass canes, washing of the medical containers, siliconization, assembling of the tip including a needle onto the barrel of the medical containers, assembling of the tip cap onto the needle, and visual inspection of the medical container. These steps result in medical containers barrels, optionally with a flange and a tip, and optionally a printed volumetric scale. The obtained medical containers are ready to be arranged in a nest.

Even if the marking of the medical container may be implemented before any of the manufacturing steps, said marking is preferably implemented after the annealing step.

Advantageously, the mark which represents a UDI may be implemented on and/or within, preferably within the material of the medical container. Preferably, the marking is performed as soon as possible in the manufacturing process, taking into account possible technical limitations (e.g. heat resistance of the marking). For example, when the marking is performed with a femtosecond laser, the marking is carried out after the annealing since the femtosecond laser marking would not sustain the annealing temperatures. However, in case of enamel sintering, the marking may be performed before annealing.

According to a preferred embodiment, the mark is laser-marked within the material of the medical container with a femtosecond laser. When a needle is intended to be assembled to the medical container, the marking is performed after the annealing but before the assembly of the needle, mainly because in that way, the marking is performed as early as possible, thereby allowing the tracking the container transformations as early as possible.

During forming and annealing steps, the data written in the data storage system and linked to barrel UDI may include:
  data relative to the forming station: machine settings, dimensional control, date, manufacturing station identifier, external temperature, raw material batch number;
  data relative to the annealing step: annealing oven temperature profile, date, etc.;
  data relative to the needle assembly/intermediate packaging: type of glue used, gluing process key process input variables, cosmetic and dimensional control results.

After these first manufacturing steps, the medical containers are washed with an appropriate fluid, such as water, in a cleaning step. Preferably, the water that is used in water for injection (acronym WFI), which is commonly used in food, chemistry, and pharmaceutical industries. Water for injection is purified water that is free of particles and bacteria.

The cleaned medical containers are then subjected to a siliconization step.

In more details, the inner part of the barrels of the medical containers is siliconized, which consists of a deposition of a thin film of silicone onto at least the inner surface of the barrel.

A tip cap may then be assembled onto the tip of the medical containers, so as to cover the needle.

During these manufacturing steps, the data written in the data storage system may include:
  data relative to the manufacturing station: type of apparatuses used, and preferably their settings, for carrying out the cleaning, sterilization, and/or assembly, date, manufacturing station identifier, external temperature, raw material batch number;
  data relative to the cleaning step: type of cleaning fluid used, temperature of the cleaning fluid, cleaning time, number of cleaning cycles;
  data relative to the siliconization step: type of silicone used, temperature of siliconization, flow rate of the silicone, siliconization time.

Step M4 of the method of the disclosure comprises placing the medical containers implemented with a mark into a nest.

The nest comprises at least one remotely readable and writable electronic component. The remotely readable and writable electronic component is preferably embedded in the nest, which prevents its deterioration. Advantageously, the remotely readable and writable electronic component may also comprise an UDI associated with the nest.

During step M5, i.e. when the medical containers are all arranged in the nest, a reader/writer writes all the UDI associated with each of the medical containers in the remotely readable and writable electronic component embedded in the nest.

Then step M6 may occur during each processing step of the nest. Thus, step M6 may either occur at the beginning, in the middle or at the end of the processing step of the nest.

During step M6, the data associated to the processing steps of the nest may be transferred from the storage device to the remotely readable and writable electronic component of the nest. The nest thereby may contain all the information relative to the processing of the medical containers up to their packaging in said nest. These data may also be transferred to another storage device different than the one previously used.

The processing steps of the nest may be at least one of the following
- sterilization of the nest and of each of the medical containers arranged in the nest;
- filling each medical container arranged in the nest with a pharmaceutical composition;
- stoppering of each of the medical containers;
- conveying the nest to an inspection spot wherein each of the medical containers may be inspected;
- storing of the nest into a tub for intermediate storage and/or shipment.

The above-mentioned steps may be implemented either at the manufacturer's place, or at the customer's place.

Advantageously, the nest may be positioned into a tub, and a film is placed to cover the upper opening of the tub containing the nest, so as to close the tub. The film may be in any appropriate material showing good mechanical resistance and sealing properties. Film in polyethylene are particularly suited for that purpose, especially Tyvek® which is a nonwoven synthetic material made from polyethylene fibers.

The tubs are placed into one or more header bags which are then sealed. The header bags are then placed into cases which are labelled, and the cases are placed onto pallets.

Typically, the data involved in the processing steps of the first layer of packaging may include:
- data relative to the packaging station: type of apparatuses used, and preferably their settings, for carrying out the placement of the containers into the nest, the placement of the nest into the tub, and the placement of the tub into the header bag, date, manufacturing station identifier, external temperature, raw material batch number;
- data relative to the placement of the containers into the nest: features of the nest;
- data relative to the placement of the nest into the tub: features of the tub, features of the film such as the constitutive material of the film;
- data relative to the placement of the tub into the header bag: features of the header bag.

The pallets may then be moved to a sterilization chamber in order to sterilize them. The sterilization is preferably performed with ethylene oxide or steam.

When present, the sensors of the first layer of packaging may record physical data relative to the sterilization of the medical containers. These physical data, called sensor data, include for example: temperature, humidity, pressure, and exposition time. These data, called sensors data, may be transferred from the remotely readable and writable electronic component to the storage device.

At any time of the processing step of the first layer of packaging, the data contained in the remotely readable and writable electronic component tag of the first layer of packaging may be transferred from the remotely readable and writable electronic component to the storage device.

These data may include:
- the UDI of the first layer of packaging, and/or
- the UDI of the medical containers contained in the first layer of packaging, and/or
- the data relative to the manufacturing steps of the medical containers; and/or
- the data relative to the processing steps of the first layer of packaging.

As such, the manufacturer and the customer may have access to several of the above-mentioned data, or to all the above-mentioned data, and thus they may have a full traceability of the medical containers and of the first layer of packaging, during the whole manufacturer processing.

When present, the sensors of the first layer of packaging may record physical data relative to the shipping of the medical containers from the manufacturer to the client, i.e. during the transportation from the manufacturer to the customer. These physical data include for example: temperature, humidity, and vibration.

The customer may perform quality tests before filing of the medical containers. The containers that pass the tests may proceed to the filling step, whether those that fail are rejected.

The quality process data include data relative to the tests carried out by the customer to determine the conformity of the medical containers in view of standards.

The customer may proceed to the unpacking of the tub in order to be able to fill them with a pharmaceutical composition. The nest containing the medical containers may be directly positioned onto the filling chain.

The data involved in these steps may include:
- data relative the filing station: type of apparatuses used, and preferably their settings, for carrying out the filing, date, filing station identifier, external temperature;
- data relative to the pharmaceutical composition: type of pharmaceutical composition, temperature, pressure, viscosity.

The customer may remove the filled medical containers from the nest, performs a visual quality inspection of the medical containers, and put the inspected medical containers back into the nest.

The double marking of both the medical containers and the corresponding first layer of packaging according to the disclosure is particularly useful here, since it allows for keeping traceability of the medical containers and their corresponding first layer of packaging when said medical containers are separated from the first layer of packaging.

The containers that pass the visual tests may be put back into the nest, while those that fail are rejected.

The data involved in this step may include:
- the updated status of the medical containers (accepted/rejected),
- data relative to the visual tests carried out by the customer to determine the conformity of the medical containers in view of standards.

The medical containers that pass the visual inspection test may be stored in a cold environment before use or transportation.

For storage, the medical containers may be transferred from the nest to another one, called "second nest", which may also comprise a remotely readable and writable electronic component (e.g. an RFID tag) configured for storing the UDI of the medical containers and for writing and/or reading data relating to the processing of the medical containers.

When present, the sensors of the nest may record physical data relative to the cold storage of the medical containers. These sensor data include for example: temperature, humidity, pressure, and in and out storage date.

The tubs containing the nests may be transported to a secondary packaging plant.

When present, the sensors of the nest may record physical data relative to the transportation of the medical containers, when the tubs are out of the cold chain. These sensor data include for example: temperature, humidity, and pressure.

Where appropriate, the sensors data are transferred from the remotely readable and writable electronic component to the storage device.

Then, the medical containers may be removed from their nests and then packaged into a secondary packaging.

The invention claimed is:

1. A system for tracking data comprising:
a plurality of medical containers received in a first layer of a packaging;
at least one mark being implemented on and/or within a material of each medical container and representing a corresponding unique device identifier (UDI) for each respective medical container;
a remotely readable and writable electronic component encased within the first layer of packaging such that the remotely readable and writable electronic component is isolated from an environment external to the first layer of packaging, the remotely readable and writable electronic component being configured for:
storing the UDI of each medical container received in the first layer of packaging,
writing data relating to the processing of the medical containers, and
writing data relating to the processing of the first layer of packaging; and
at least one sensor encased within the first layer of packaging, the at least one sensor configured to record physical data relating to the first layer of packaging and transfer the recorded physical data to the remotely readable and writable electronic component.

2. The system for tracking data according to claim 1, wherein the first layer of packaging is a nest or a tub.

3. The system for tracking data according to claim 1, wherein the remotely readable and writable electronic component comprises a corresponding unique device identifier relating to the first layer of packaging.

4. The system for tracking data according to claim 3, further comprising a data storage system configured for storing data relating to the processing of the medical container, said data being associated with the UDI of each medical container and optionally with the UDI of the first layer of packaging.

5. The system for tracking data according to claim 1, wherein the at least one mark is optical.

6. The system for tracking data according to claim 1, wherein the remotely readable and writable electronic component is selected from the group consisting of a RFID tag, a ultra wide-band real-time location system (RTLS), a wifi-enabled module, a Bluetooth-enabled module, a ZigBee-enabled module and an infrared-enabled module.

7. The system for tracking data according to claim 5, wherein the at least one mark is selected from the group consisting of a 1D mark, such as a bar code, a 2D mark such as a Data Matrix or a QR code, and a text.

8. The system for tracking data according to claim 6, wherein the remotely readable and writable electronic component is a RFID tag which comprises an RFID chip and an antenna connected to the chip.

9. The system for tracking data according to claim 1, wherein the data relating to the processing of the first layer of packaging includes manufacturing data.

10. The system for tracking data according to claim 1, wherein the data relating to the processing of the first layer of packaging includes transportation data.

11. The system for tracking data according to claim 1, wherein the data relating to the processing of the first layer of packaging includes sterilization data.

12. The system for tracking data according to claim 1, wherein the at least one sensor comprises a temperature sensor.

13. The system for tracking data according to claim 1, wherein the at least one sensor comprises a humidity sensor.

14. The system for tracking data according to claim 1, wherein the at least one sensor comprises a pressure sensor.

15. The system for tracking data according to claim 1, wherein the at least one sensor comprises a vibration sensor.

16. The system for tracking data according to claim 1, wherein the at least one sensor comprises a movement sensor.

17. The system for tracking data according to claim 9, wherein the manufacturing data comprises at least one of: a machine setting, a manufacturing station identifier, or a raw material batch number.

18. The system for tracking data according to claim 1, wherein the data relating to the processing of the first layer of packaging comprises at least one of: a machine setting, a packaging station identifier, or a raw material batch number.

* * * * *